Uda et al.

United States Patent [19]

[11] Patent Number: 4,910,133
[45] Date of Patent: Mar. 20, 1990

[54] DIAGNOSTIC TEST DRUG COMPRISING MONOCLONAL ANTIBODY TO HUMAN COPPER ZINC-SUPEROXIDE DISMUTASE AND DIAGNOSTIC TEST METHOD USING THE SAME

[75] Inventors: Taizo Uda, Ube; Schirou Noji, Tokyo; Takashi Usagawa, Ogouri; Kazuhiro Umeda, Ube, all of Japan

[73] Assignee: Ube Industries, Limited, Ube, Japan

[21] Appl. No.: 901,006

[22] Filed: Aug. 27, 1986

[30] Foreign Application Priority Data

Aug. 29, 1985 [JP] Japan ................................ 60-188458

[51] Int. Cl.⁴ ...................... G01N 33/53; G01N 33/48; C12Q 1/26
[52] U.S. Cl. .......................................... 435/7; 435/25; 436/64; 436/76; 436/518; 436/531; 436/548; 436/813; 424/85.8
[58] Field of Search ..................... 435/7, 25, 68, 172.2, 435/240.2; 436/518, 64, 547, 548, 76, 813, 531, 513; 424/85, 86, 85.8, 88

[56] References Cited

U.S. PATENT DOCUMENTS 4,376,110  3/1983  David et al. ..................... 436/513
4,657,853  4/1987  Freytag et al. ..................... 435/7

FOREIGN PATENT DOCUMENTS 0007560  1/1983  Japan ..................................... 435/7
0086098  5/1983  Japan ..................................... 435/7
2089979  3/1982  United Kingdom ..................... 435/7

OTHER PUBLICATIONS

Getzoff et al., in Superxide and Superoxide Dismutase in Chemistry, Biology and Medicine, (1986), 135–140.
Chemical Abstract 97(11) 87493n.
Chemical Abstract 103: 176901d.
Biological Abstract 81(11): 100970.
Derwent Abstract C86-125308.
Kensler et al., Science, vol. 221, No. 4605, (1983), pp. 75–77.
Robbins, Pathologic Basis of Disease, (1974), pp. 924–927.
Baret et al., Biochem. Biophys. Res. Comm., vol. 88, No. 2, (1979), pp. 337–345.
Chemical Abstract 109: 31413.
Chemical Abstract 108: 14587.

Primary Examiner—Robert J. Warden
Assistant Examiner—Carol A. Spiegel
Attorney, Agent, or Firm—Foley & Lardner, Schwartz, Jeffery, Schwaab, Mack, Blumenthal & Evans

[57] ABSTRACT

There is disclosed a measurement reagent for a human Cu.Zn-superoxide dismutase (SOD) which comprises an anti-human Cu.Zn-SOD monoclonal antibody labelled with an enzyme, a method for measuring a human Cu.Zn-SOD which comprises measuring the human Cu.Zn-SOD with the measurement reagent for the human Cu.Zn-SOD, and an anti-human Cu.Zn-SOD monoclonal antibody by the enzyme-linked immunosorbent assay according to the sandwich method, a diagnostic test drug for a human cancer of the stomach which comprises the measurement reagent and a method for diagnosing and testing a human cancer of the stomach which comprises measuring the human Cu.Zn-superoxide dismutase with the measurement reagent, and an anti-human Cu.Zn-superoxide dismutase monoclonal antibody by the enzyme-linked immunosorbent assay according to the sandwich method.

6 Claims, 5 Drawing Sheets

DIAGNOSTIC TEST DRUG COMPRISING MONOCLONAL ANTIBODY TO HUMAN COPPER ZINC-SUPEROXIDE DISMUTASE AND DIAGNOSTIC TEST METHOD USING THE SAME

BACKGROUND OF THE INVENTION

This invention relates to a diagnostic test drug comprising monoclonal antibody to human copper.zinc-superoxide dismutase and a diagnostic test method using the same, and more specifically to a diagnostic test drug comprising monoclonal antibody to human copper.-zinc-superoxide dismutase which is capable of conducting diagnosis of various diseases with good precision and good reproducibility and a diagnostic test method using the same.

Superoxide dismutase (SOD) is an enzyme distributed very widely in biological world and catalyzes the reaction as shown below which disproportionates the superoxide anion radicals ($O_2^-$) which are principal molecular species of toxic oxygen:

$$O_2^- + O_2^- + 2H^+ \rightarrow H_2O_2 + O_2$$

SOD is classified into the three kinds of Cu.Zn—SOD (a dimer having a molecular weight of about 32,000), Mn—SOD and Fe—SOD (both are dimers having a molecular weight of about 40,000). In the respective human tissues, Cu.Zn—SOD is confirmed in the cytoplasm portion and Mn—SOD in the matrix portion of mitochondrion.

For Fe—SOD and Mn—SOD, high homology can be seen in their amino acid sequences between biological species and evolutional analogical relationship is estimated therebetween. In contrast, Cu.Zn—SOD is inherent in eucaryote and has a different amino acid sequence from other kinds of SOD. The Cu.Zn—SOD has been clinically recognized to have anti-inflammatory action, and the Cu.Zn—SOD derived from bovine is now under progress of development as therapeutical agent for inflammatory diseases such as chronic rheumatism. However, as a pharmaceutical, the Cu.Zn—SOD derived from human is considered to be more excellent than that derived from bovine in aspect of antigenicity. Accordingly, when an anti-human Cu.Zn—SOD antibody having very high specificity is used for purification of Cu.Zn—SOD contained in human organs (e.g. placenta) or human Cu.Zn—SOD produced in microorganism by genetic manipulation, the purification step can be by far easier than the conventional method and further still higher purity can be obtained.

On the other hand, Sawaki, Sugiura et al examined about the relationship between measured values of human serum SOD and various diseases with the use of antiserum to human SOD obtained from rabbit (reported in the 55th general meeting of Biochemical Society of Japan). According to their experimental results, the Cu.Zn—SOD value in human serum becomes some 10-fold in kidney failure, particularly uremia, and is increased to several fold in hepatitis, diabetes accompanied with complications, fibroid lung, etc. The above facts indicate that Cu.Zn—SOD can be a marker for diagnosis of these diseases.

The present inventors have studied intensively in order to develop a method for conducting diagnosis of the above various diseases with good precision and good reproducibility, and consequently found that the method in which an amount of Cu.Zn—SOD in human serum can be detected with good precision by use of monoclonal antibody specific for the human Cu.Zn—SOD can be effected for diagnosis of the cancer of the stomach to accomplish the present invention.

SUMMARY OF THE INVENTION

The present invention provides a diagnostic test drug comprising a monoclonal antibody and an enzyme-labelled monoclonal antibody recognizable human Cu.Zn—SOD (copper.zinc-superoxide dismutase) with extremely high specificity and a diagnostic test method for human Cu.Zn—SOD.

DESCRIPTION OF THE PREFERRED EMBODIMENTS

The monoclonal antibody to be used in the present invention can be prepared according to the method as described below.

That is, in the first place, SOD (purity: 95% or higher) derived from human erythrocytes is immunized into, for example, BALB/c mouse, etc., and then the spleen is extirpated, followed by fusion with mouse myeloma cells of SP2 or NS-1 with the use of polyethylene glycol to obtain a hybridoma in conventional manner. And, in order to obtain a large amount of monoclonal antibodies, a predetermined amount of the hybridoma is transplanted into the abdomen of mouse previously administered with pristane (2,6,10,14-tetramethylpentadecane), and thereafter the ascites is collected 1-2 weeks later. The ascites collected is purified by use of an ion exchange chromatography or ammonium sulfate fractionation. Also, the monoclonal antibody of the present invention can be prepared according to the method in which the above hybridoma is cultured in a large amount in a culturing tank.

The monoclonal antibody of the present invention thus obtained has the following properties.

1. It does not react with human albumin, human α-globulin and human γ-globulin at all.
2. It reacts specifically with a human type Cu.Zn—SOD as a matter of course, and when the liver cytosol is stained with the present antibody according to the Western blotting method, only Cu.Zn—SOD in the liver cytosol is selectively stained.

The diagnostic test drug can be used widely for immunological assay of Cu.Zn—SOD, for example, assay according to double diffusion within agar gel, one-dimensional immunodiffusion, immunoelectrophoresis, latex agglomeration, erythrocyte agglomeration reaction, radioimmunoassay, enzyme-linked immunosorbent assay (ELISA), etc.

It is possible to measure a Cu.Zn—SOD in serum or urine by use of these methods, as a matter of course. Further, cells containing Cu.Zn—SOD can be detected and diagnosed according to the method such as peroxidase-labelled antiperoxidase (PAP) staining, etc.

For example, to explain about the diagnostic test method according to the ELISA method, a plurality of purified monoclonal antibodies are mixed in appropriate amounts and apportioned into a 96-well plate for immunoassay and held at 4° C. overnight. Next, after each well in this plate is washed with a buffer, a sample containing Cu.Zn—SOD is added and incubated at 30° C. for 3 hours. Subsequently, after each well is again washed with a buffer, a monoclonal antibody labelled with enzyme is added and incubated at 30° C. for 2 hours. Then, after washing, a substrate solution is added and after incubation for a predetermined time, absorbance at a wavelength showing maximum absorbance is measured by a spectrophotometer to determine the quantity, and at the same time, an amount of human Cu.Zn—SOD in the sample can be determined by using the prepared calibration curve.

The enzyme for use to label the human Cu.Zn-superoxide dismutase of the present invention may be mentioned, for example, peroxidase, alkaline phosphatase, $\beta$-galactosidase, catalase, glucose oxidase, lactose oxidase, alcohol oxidase and monoamine oxidase.

The monoclonal antibody to be used in the present invention can be labelled in a conventional manner with radioisotope ("RI"), enzyme, fluorescent group, metal sol, etc.) depending on the purpose in carrying out measurement.

The diagnostic test drug according to the present invention can react specifically with Cu.Zn—SOD not only in human serum or urine but also in cytoplasm, and therefore it can be known the relationship between the amount of human Cu.Zn—SOD and various diseases of human by utilizing the monoclonal antibody. Thus, in the present invention, it is found that the measurement of the amount of human Cu.Zn—SOD utilizing the present monoclonal antibody is effective for diagnosis test of cancer of the stomach.

The present invention will be described in more detail by referring to the following Reference examples, Examples and Comparative example.

REFERENCE EXAMPLE 1

Preparation of anti-human Cu.Zn—SOD monoclonal antibody (1) Immunization

An amount of 0.25 ml of PBS (Phosphate Buffered Saline) having 100 $\mu$g of human Cu.Zn—SOD dissolved therein and 0.25 ml of Freund's complete adjuvant were mixed to prepare an emulsion, and 0.5 ml of the emulsion was administered intraperitoneally to BALB/c mouse (male, 7 weeks old). Three weeks later 0.5 ml of an emulsion prepared by mixing 0.25 ml of PBS having 100 $\mu$g of the same antigen dissolved therein and 0.25 ml of Freund's incomplete adjuvant was administered intraperitoneally. Further, 3 weeks later, as the final immunization, 0.5 ml of PBS having 100 $\mu$g of the same antigen dissolved therein was administered into the tail vein.

(2) Cell fusion

On the fourth day after the final immunization, the spleen of the mouse was extirpated, washed in a laboratory dish containing Hanks' solution under ice-cooling, transferred into MEM (Eagle Minimum Essential Medium), divided into 4 equal portions and loosened by a pair of tweezers. The floating lymphocytes thus obtained were washed three times with MEM (1,000 rpm, 5 minutes) and suspended in RPMI 1640 to provide spleen lymphocytes to be used for cell fusion. Next, $2 \times 10^7$ 8-AG (8-azaguanine) resistant myeloma cells (NS-1 or SP2) previously prepared and $2 \times 10^8$ spleen lymphocytes were mixed, the supernatant was removed at room temperature (1,000 rpm, 5 minutes) and the pellet was loosened by tapping the centrifugal tube. Into this was added 1 ml of 45% PEG 4000 heated to 37° C. over one minute, and the mixture was left to stand at 37° C. for 6 minutes. Then, RPMI 1640 heated to 37° C. was gradually added at the rate of 5 ml/min. over 3 minutes, until the mixture was finally made up to 50 ml, and the mixture was subjected to centrifugation at room temperature (1,000 rpm, 5 minutes), followed by removal of the supernatant. This was suspended in 200 ml of HAT medium previously heated to 37° C. (15% FCS-RPMI 1640 medium containing $1 \times 10^{-4}$M hypoxanthine, $4 \times 10^{-7}$M aminopterin, $1.6 \times 10^{-5}$M thymidine), and apportioned each in 100 $\mu$l to the respective wells of a 96-well microtiter well to carry out cultivation.

(3) HAT selection

On the 4th day after cell fusion, each 50 $\mu$l of HAT medium was added into each well, and ELISA was conducted from about the 10th day when growth of hybridoma was recognized, and 50 $\mu$l of HT medium (15% FCS-RPMI 1640 medium containing $1 \times 10^{-4}$M hypoxanthine, $1.6 \times 10^{-5}$M thymidine, where "FCS" denotes fetal calf serum) was added into the well where antibody production was recognized, and thereafter those hybridomas were acclimatized in 15% FCS-RPMI 1640 medium under observation of the growth thereof.

(4) Selection of hybridoma

Over 1 to 3 weeks from initiation of cultivation, it was assayed by ELISA whether anti-human Cu.Zn—SOD antibody was contained in the culture supernatant in the well in which cell growth was recognized.

First, into the respective wells of a 96-well U-bottomed ELISA plate, each 50 $\mu$l of human Cu.Zn—SOD (10 $\mu$g/ml) was apportioned and left to stand overnight at 4° C. Each well was washed three times with washing liquid (PBS containing 0.1% TWEEN 20 (trade name, produced by Katayama Kagaku Kogyo), and each 50 ml of the above culture supernatant was apportioned thereinto and left to stand at room temperature for 2 hours (for the supernatant as the negative control, a cultured product of a mixture of spleen lymphocytes and myeloma cells before fusion cultured similarly was used). Next, these wells were washed three times, each 50 $\mu$l of peroxidase-labelled anti-mouse (IgG, IgM, IgA) antibody solution was apportioned into each well and left to stand at room temperature for 2 hours. These wells were washed four times, each 100 $\mu$l of a substrate solution (prepared by dissolving 20 mg of o-phenylenediamine and 10 $\mu$l of 35% $H_2O_2$ in 50 ml of 0.1M citrate buffer of pH 5.0) into each well and left to stand at room temperature for 30 minutes under shielding from light with aluminum foil. Finally, the enzyme reaction was stopped by apportioning each 50 $\mu$l of 2N sulfuric acid into each well, and absorbance at 492 nm was measured. Anti-human Cu.Zn—SOD antibody producing hybridoma was considered to exist in the well from which supernatant exhibiting positive enzyme activity was taken. As the result of assay of the culture supernatant in the cell grown well as described above, the (antibody producing well number/ELISA well number) was found to be (85/1566) in the case of using NS-1 as the myeloma cell and (54/329) in the case of using SP2.

(5) Establishment of hybridoma strain

By use of 15% FCS-RPMI 1640 medium, the hybridoma in the antibody producing well as described in (4) was subjected to cloning according to the limiting dilution method. For cultivation, a 96-well microtiter well was used and $10^7$/ml thymus cells of BALB/c mouse were used as the supporting cells, and the hybridoma was cultured at 1 cell/100 μl/well. From about the 10th day after cultivation, the supernatant in the well which appears to contain a single colony was sampled and subjected to ELISA by use of human Cu.Zn—SOD, and the sample in which antibody was recognized was further examined for reactivity with other antigens (human albumin, human globulin, etc.). Thus, 6 strains were selected (S-1, S-2, S-4, S-6, N-4, N-6; applied to deposition at Agency of Industrial Science and Technology, Japan on Feb. 7, 1980 but received a Notice of refusal to receive deposition on Feb. 13, 1980) and subjected to recloning (listed in Table 1).

(6) Determination of class.sub-class of anti-human Cu.Zn—SOD monoclonal antibody Determination of class.sub-class of the immunoglobulin produced by each hybridoma was conducted according to the method of ELISA as described in Reference example 1 (4) by use of a peroxidase-labelled antibody (affinity purified antibody to $IgG_1$, $IgG_{2a}$, $IgG_{2b}$, $IgG_3$, IgM, IgA) specific for each class.sub-class of the monoclonal antibodies produced by the 6 strains, the antibodies of the two strains were IgM and those of the four strains were $IgG_1$ (listed in Table 1). The types of the Light chain of the respective antibodies were all κ type.

(7) Production of monoclonal antibody

Production of antibody was carried out by flask culturing or intraperitoneally in mouse. According to flask culturing, the hybridoma obtained by culturing in a 15% FCS-RPMI 1640 medium was cultured in only RPMI 1640 immediately before death (monoclonal antibody existed in an amount of 10 to 50 μg/ml in the supernatant obtained by centrifugation). On the other hand, production in mouse abdomen for obtaining a large amount of antibody was carried out by administering intraperitoneally $10^6$ to $10^7$ hybridomas floated in RPMI 1640 into BALB/c mouse (male, 6 to 10 weeks old, administered intraperitoneally with 0.5 ml of pristane 2 to 3 weeks before). Marked increase of mouse body weight was recognized from about one week later, and ascites was taken out suitably after 1 to 3 weeks.

REFERENCE EXAMPLE 2

Specificity of antibody

Specificity of the monoclonal antibody produced by the 6 strains as described in Reference example 1 (5) was examined from reactivities with human Cu.Zn—SOD, human Mn—SOD, bovine SOD, canine SOD, human albumin, human α-globulin, human γ-globulin, etc. (listed in Table 1). The reaction between these monoclonal antibodies with antigen was carried out according to the method of ELISA as described in Reference example 1 (4).

As shown in Table 2, everyone of the monoclonal antibodies produced by the 6 strains does neither react with albumin and globulin which are main components of human serum proteins nor react human Mn—SOD. The antibodies of the 6 strains specifically react with human Cu.Zn—SOD, and one strain (N-6) of them reacted with SOD of bovine and canine.

TABLE 1

| Class.sub-class of monoclonal antibody | | | |
|---|---|---|---|
| Myeloma cell used for fusion | Strain name | Class.sub-class of produced antibody | Type of L chain |
| SP2 | S-1 | M | κ |
|  | S-2 | $G_1$ | κ |
|  | S-4 | M | κ |
|  | S-6 | $G_1$ | κ |
| NS-1 | N-4 | $G_1$ | κ |
|  | N-6 | $G_1$ | κ |

TABLE 2

| | Specificity of monoclonal antibody | | | | | | |
|---|---|---|---|---|---|---|---|
| | Antigen | | | | | | |
| Antibody | Human Cu.Zn—SOD | Human Mn—SOD | Bovine SOD | Canine SOD | Human albumin | Human α-globulin | Human γ-globulin |
| S-1 | +++ | — | ± | ± | — | — | — |
| S-2 | +++ | — | ± | ± | — | — | — |
| S-4 | +++ | — | ± | — | — | — | — |
| S-6 | +++ | — | — | — | — | — | — |
| N-4 | +++ | — | — | — | — | — | — |
| N-6 | +++ | — | ++ | + | — | — | — |

(Extent of reaction between antigen and antibody: +++ > ++ > + > ± > —)

EXAMPLE 1

Of the monoclonal antibodies obtained in Reference example, N-4 was used and labelled with horseradish peroxidase according to the method of NAKANE et al. (NAKANE, R. K., and KAWAOI, A. J. Histochem. Cytochem., 22, 1084, 1974).

To a 96-well immunoplate, each 100 μl of the mixed solution of monoclonal antibody (mixing ratio of S-2:S-6:N-4:N-6=1:1:1:1) was added and incubated at 4° C. overnight. Next, excessive binding sites were covered with 10% bovine serum. Each 100 μl of the samples containing various concentrations of SOD was added and incubated at 30° C. for 3 hours. Next, after thoroughly washed with physiological saline, each 100 μl of the above peroxidase-labelled anti-SOD antibody appropriately diluted was added and incubated at 30° C. for 2 hours.

Figure 1:
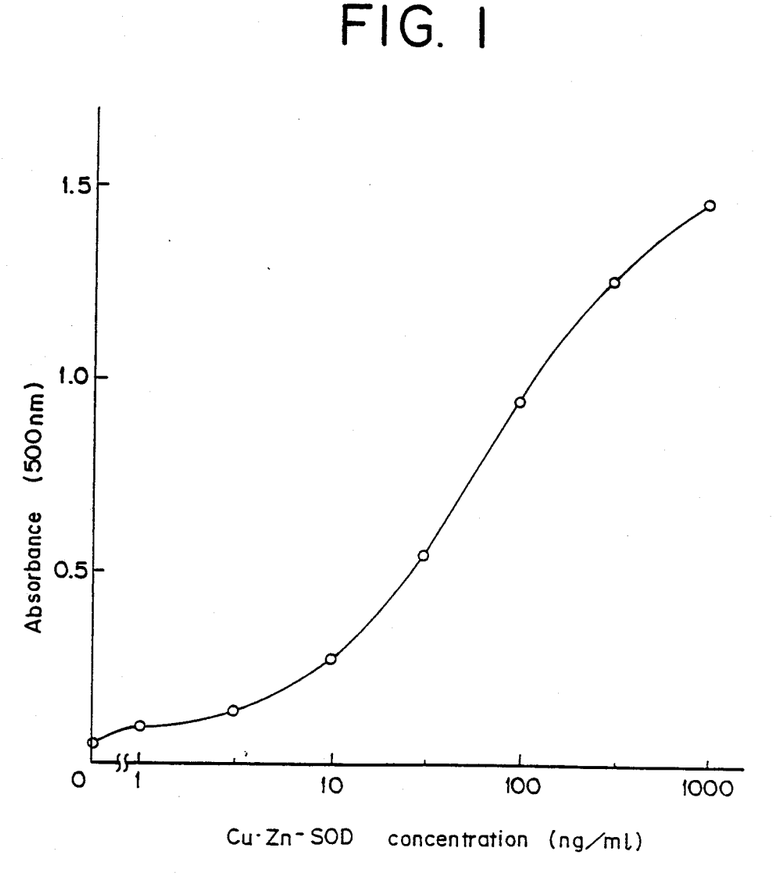
FIG. 1, FIG. 2, FIG. 3 and FIG. 4 show examples of calibration curves for measurement of Cu.Zn—SOD in samples by use of the diagnostic test drug according to the present invention.

Further, after washing with physiological saline, activity of peroxidase was detected with o-phenylenediamine by use of hydrogen peroxide as the substrate, and absorbance was measured to obtain a calibration curve of the human Cu.Zn—SOD as shown in FIG. 1. By use of the calibration curve, SOD concentration in a sample of unknown concentration could be determined.

Also, by use of the calibration curve such as the one shown in FIG. 1, the addition recovery test of SOD was conducted to obtain the results shown in Table 3.

TABLE 3

| Addition-recovery test of SOD | | | |
|---|---|---|---|
| Final concentration added (ng/ml) | Absorbance | Reading on calibration cruve | Recovery (%) |
| 111 | 0.969 | 110 | 99 |
| 36 | 0.599 | 40 | 110 |

EXAMPLE 2

The anti-human Cu.Zn—SOD monoclonal antibody was bound onto a solid phase carrier of polystyrene beads, and a calibration curve was prepared similarly as in Example 1.

After polystyrene beads (produced by Wako Junyaku K.K., 3.2 mm) were soaked in 10% SCAT 20× (trade name, produced by Daiichi Kogyo Seiyaku K.K.) for several days and thereafter washed well with tap water and distilled water. The polystyrene beads were soaked in PBS (Phosphate Buffered Saline) containing the anti-human Cu.Zn—SOD monoclonal antibody (15 μg/ml, S-2:S-6:N-4:N-6=1:1:1:1) at 4° C. overnight to immobilize the monoclonal antibody on the polystyrene beads. Subsequently, after washing twice with PBS containing 0.1% TWEEN 20 (trade name, produced by Katayama Kagaku Kogyo) and soaked in PBS solution containing 10% CS (calf serum) to effect blocking. This was again washed and then stored in PBS solution containing 1% bovine serum albumin ("BSA") and 0.1% $NaN_3$ to be brought into the state available at any time.

Figure 2:
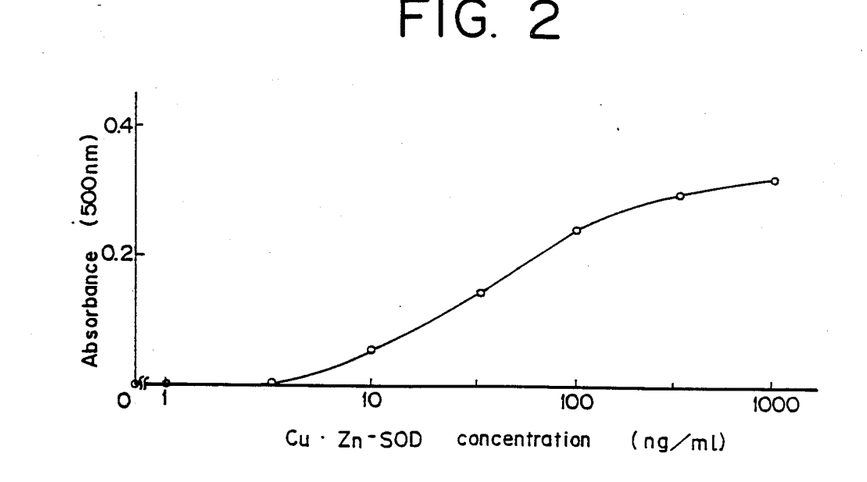

The polystyrene beads having the monoclonal antibody immobilized thereon thus prepared was taken out in necessary amount, and the same operation as in Example 1 was carried out to prepare a calibration curve of the human Cu.Zn—SOD. The calibration curve obtained is shown in FIG. 2.

EXAMPLE 3

Figure 3:
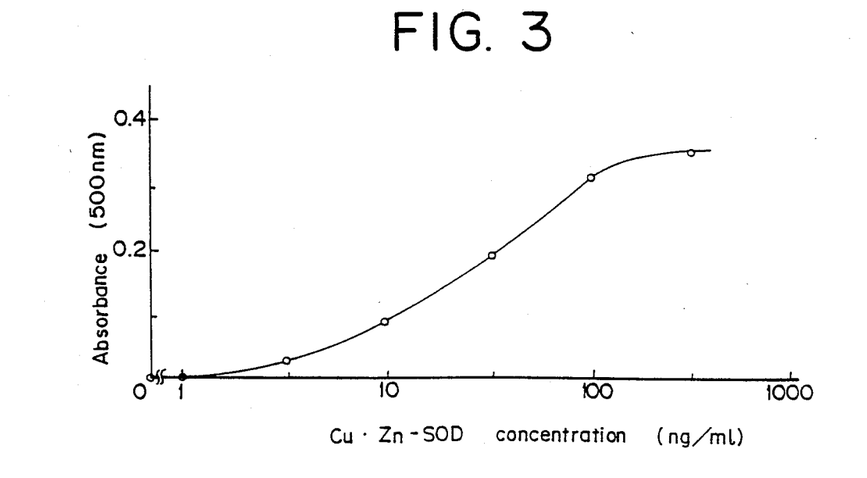

According to the same procedure as in Example 2 except for using S-2, S-6 (S-2:S-6=1:1) as the monoclonal antibodies, calibration curve of the human Cu.Zn—SOD was prepared. The calibration curve obtained is shown in FIG. 3.

COMPARATIVE EXAMPLE 1

Figure 6:
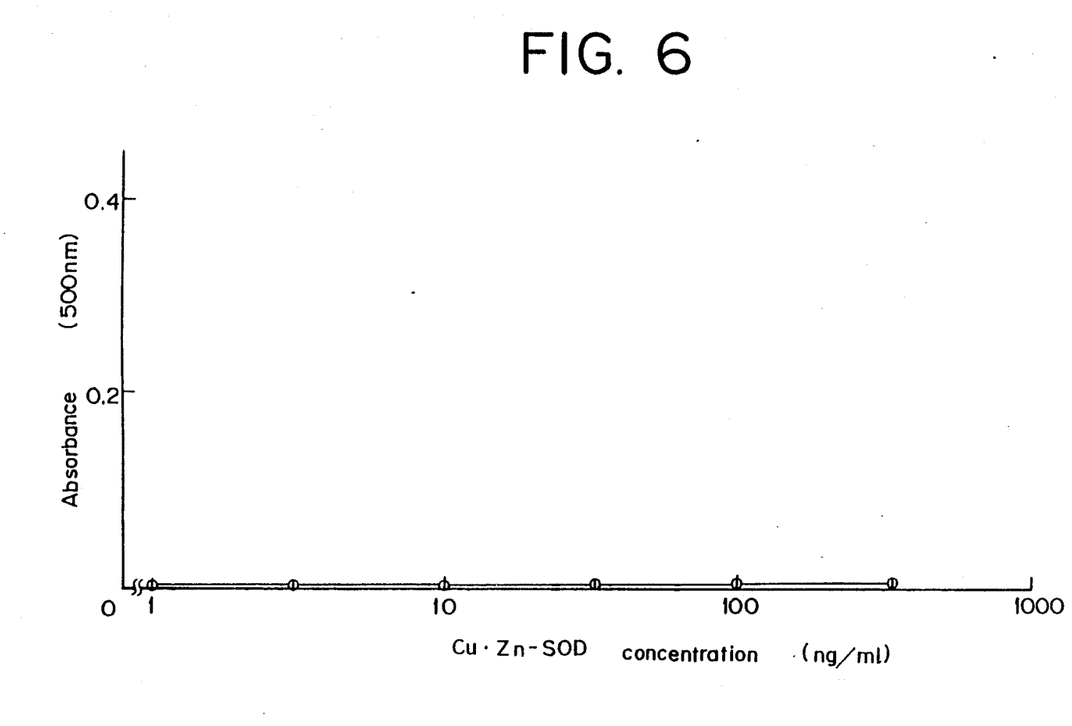
FIG. 6 shows a calibration curve of Comparative example.

A calibration curve was attempted to be prepared according to the same procedure as in Example 2 except for using N-4 as the monoclonal antibody. However, in this case, no calibration curve could be drawn as shown in FIG. 6.

Thus, by use of the calibration curve as obtained in Example 1, 2 and 3, the concentration of a human type Cu.Zn—SOD in a sample of unknown concentration can be determined.

EXAMPLE 4

Figure 4:
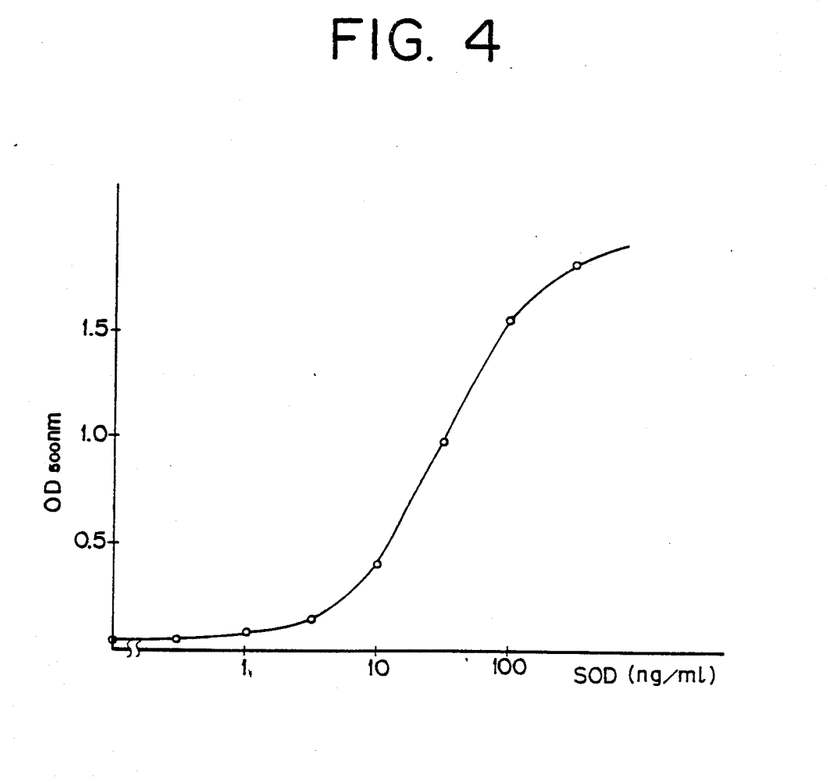

According to the same procedure as in Example 1 except for using N-4 as the monoclonal antibody and N-6 as the monoclonal antibody labelled with peroxidase by the method of NAKANE et al, calibration curve of the human Cu.Zn—SOD was prepared. The calibration curve obtained is shown in FIG. 4.

EXAMPLE 5

By using sera of various cancer patients and sera of normal men, investigation was carried out in the relations between concentrations of Cu.Zn—SOD in these sera and various diseases.

These sera employed were those in which no cythemolysis (dissolution of erythrocytes and leukocytes) was observed and sufficient care has been paid during preservation.

Numbers of sera of cancer patients herein used were 4 of colorectal carcinoma, 2 of cancer of the esophagus, 3 of cancer of the cholecystis (gallbladder), 14 of cancer of the stomach and 10 of cancer of the pancreas, and numbers of sera of the normal human were 110.

The concentrations of Cu.Zn—SOD in these sera were measured by the method as described in Example 4 and a calibration curve was also prepared by the method in the same. The results are shown in FIG. 5.

Figure 5:
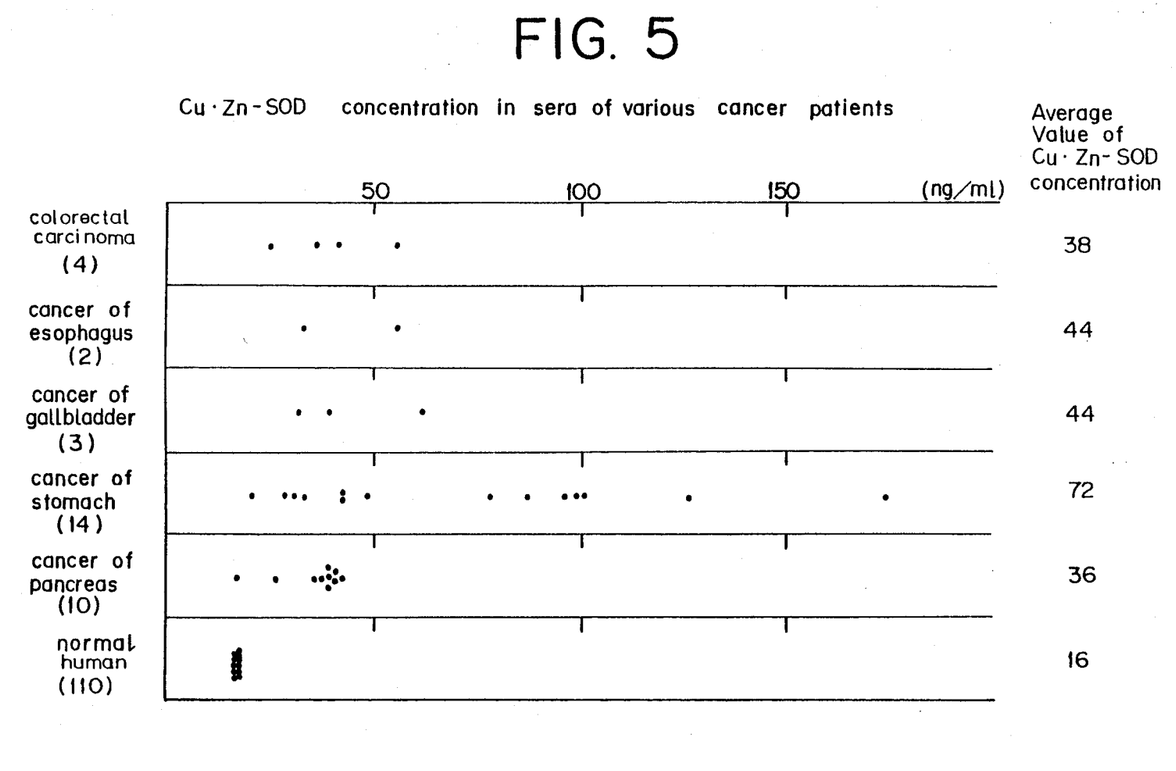
FIG. 5 shows Cu.Zn—SOD concentrations in sera of various cancer patient and normal human.

As seen from FIG. 5, in the sera of the patients of cancer of the stomach, it is clearly found that quite a number of patients showing high value of the Cu.Zn—SOD concentration has been admitted as compared with the sera of the normal human. Since such high values in the Cu.Zn—SOD concentration have not been admitted in the sera of the other patients, it can be estimated that if the concentration of the Cu.Zn—SOD is high by the method as mentioned above, he would be a cancer of the stomach. Accordingly, by the measurement of the Cu.Zn—SOD in the human serum using the monoclonal antibody specific to the human Cu.Zn—SOD, diagnostic test of the cancer of the stomach can be carried out with ease.

According to the above, it could be found that by the measurement method of the Cu.Zn—SOD using appropriate two kinds (only one of which is used by labelling with peroxidase) of the monoclonal antibodies among those specific to the human Cu.Zn—SOD of the present invention, diagnosis of the cancer of the stomach can easily be carried out. Accordingly, the fact that such a diagnosis using the monoclonal antibody can easily be carried out before carrying out the conventional medical examination by using an autoscope, an X-ray, etc., will lead to discovery of much more patients of the cancer of the stomach since increase in a number of patients to be consulted would be expected.

We claim:

1. A method for diagnosing human cancer of the stomach, comprising determining the level of human Cu,Zn-superoxide dismutase in a biological fluid sample of a human patient, wherein a diagnostically significant elevated level of human Cu,Zn-superoxide dismutase is indicative of human cancer of the stomach.

2. The method of claim 1, wherein said level of human Cu,Zn-superoxide dismutase is determined using an enzyme-linked immunosorbent assay for determining human Cu,Zn-superoxide dismutase in a biological fluid sample, comprising the steps of:

(a) contacting a biological fluid sample suspected of containing human Cu,Zn-superoxide dismutase with a solid phase to which is bound a capture polyclonal or monoclonal antibody which specifically binds human Cu,Zn-superoxide dismutase, and separating unbound components of said fluid sample;

(b) contacting said solid phase, to which is bound said human Cu,Zn-superoxide dismutase, with an enzyme-labeled probe monoclonal antibody which specifically binds human Cu,Zn-superoxide dismutase and which does not substantially cross-react with human Mn-superoxide dismutase, human alpha-globulin or human gamma-globulin, and separating unbound labeled probe; and (c) detecting the labeled probe bound to said solid phase in step (b) in order to determine the human Cu,Zn-superoxide dismutase in said fluid sample.

3. The method of claim 2, wherein said capture antibody is a murine monoclonal which specifically binds human Cu,Zn-superoxide dismutase and which binds to a different epitope on human Cu,Zn-superoxide dismutase from said at least one probe murine monoclonal antibody and does not cross-block said probe antibody.

4. The method of claim 2, wherein said probe monoclonal antibody is not cross-reactive with either bovine or canine superoxide dismutase.

5. The method of claim 2, wherein said enzyme label is selected from the group consisting of peroxidase, alkaline phosphatase, $\beta$-galactosidase, catalase, glucose oxidase, lactose oxidase, alcohol oxidase and monoamine oxidase.

6. The method of claim 2, wherein said capture antibody is a plurality of murine monoclonal antibodies each of which specifically binds to a different epitope on human Cu, Zn-superoxide dismutase from the others and each of which does not substantially cross-react with human Mn-superoxide dismutase, human alpha-globulin or human gamma-globulin.

* * * * *